United States Patent [19]

Marple et al.

[11] 4,321,822
[45] Mar. 30, 1982

[54] IMPACTOR APPARATUS

[75] Inventors: Virgil A. Marple, Maple Plain; Benjamin Y. H. Liu, North Oaks, both of Minn.

[73] Assignee: The Regents of the University of Minnesota, Minneapolis, Minn.

[21] Appl. No.: 156,667

[22] Filed: Jun. 5, 1980

[51] Int. Cl.$^3$ ............................................. G01N 15/02
[52] U.S. Cl. ...................... 73/28; 73/863.22; 55/270
[58] Field of Search ............... 73/28, 432 PS, 863.22, 73/863.23; 55/270

[56] References Cited

U.S. PATENT DOCUMENTS

| | | | |
|---|---|---|---|
| 2,894,877 | 7/1959 | Sinden | 73/28 |
| 3,518,815 | 7/1970 | McFarland et al. | 73/28 |
| 3,678,759 | 7/1972 | Schneeberger | 73/28 |
| 3,795,135 | 3/1974 | Andersen | 73/28 |
| 3,938,366 | 2/1976 | Wertlake et al. | 73/28 |
| 3,983,743 | 10/1976 | Olin et al. | 73/28 |

FOREIGN PATENT DOCUMENTS 278967  8/1970  U.S.S.R. ................................. 73/28

OTHER PUBLICATIONS

G. A. Carson et al., "High Volume Cascade Seive Impactor", *American Industrial Hygiene Ass. Journal,* pp. 262-268, May 1974.
V. A. Marple et al., "Characteristics of Laminar Jet Impactors", *Environmental Science and Technology,* vol. 8, No. 7, pp. 648-654, Jul. 1974.
V. A. Marple et al., "On Fluid Flow and Aerosol Impaction in Inertial Impactors", *Journal of Colloid and Interface Science,* vol. 53, No. 1, pp. 31-34, Oct. 1975.
V. A. Marple et al., "Inertial Impactors: Theory, Design and Use", *Fine Particles: Aerosol Generation, Measurement, Sampling and Analysis,* pp. 411-446, 1976.

Primary Examiner—Stephen A. Kreitman
Attorney, Agent, or Firm—Burd, Bartz & Gutenkauf

[57] ABSTRACT

An impactor apparatus operable to collect particles for subsequent gravimetric or chemical analysis. The apparatus has a first assembly for supporting particle impaction means and a second nozzle assembly releasably mounted on the first assembly having nozzle means for directing gas and particles to the particle impaction means. The nozzle assembly can be removed from the first assembly supporting the particle impaction means and reassembled after an impaction test on a new assembly having cleaned particle impaction means. A cover is mounted on the assembly so that the assembly, along with the particle impaction means, can be transported to the laboratory for analysis. A modification of the particle impactor apparatus has rotating table means aligned with a plurality of nozzles so that a uniform layer of particles are deposited on each of the impaction plates carried by the tables. A plurality of rotating tables are employed in series with separate nozzle means to provide a cascade inertial impactor apparatus.

38 Claims, 21 Drawing Figures

IMPACTOR APPARATUS

BACKGROUND OF INVENTION

An inertial impactor has one or more nozzles which direct a jet of gas, such as air, and particles carried by the gas to an impaction plate. The particles larger than the cut-off size of the impactor cross the streamlines and impinge upon the impaction plate. The smaller particles pass with the gas stream out of the impaction region.

Cascade impactors have been used for a number of years to collect aerosol particles. A cascade impactor has a series of nozzles with successive nozzle orifices being smaller. The smaller the nozzle orifices, the higher the velocity of gas and particles moving through the orifices. The size range of the particles collected on the impaction plate is the function of the velocity of the particles moving through the nozzle orifices. The higher the velocity, the smaller the particles that are collected on the impaction plate. The deposits of particles of these impactors are normally analyzed by microscope inspection, by weighing, or by chemical analysis to determine the chemical composition of the particles.

In general, it is the current practice to disassemble the impactor piece-by-piece each run and remove the impaction plates. New impaction plates are installed. The impactor is then reassembled piece-by-piece. This is an objectionable procedure, as the impaction plate for each stage of the impactor must be handled on disassembly and transferred to some container for further analysis. The assembly and disassembly operations are tedious and time consuming, making the use of the impactor difficult in field operations. If small deposits of particles are collected for gravimetric or chemical analysis, there is a very high probability that some of the deposits will be damaged in the changing of the impaction plates. In the cascade impactor the damage to the deposit of particles on one impaction plate would make it impossible to determine the correct size distribution of the particles.

One of the major difficulties in using impactors is that the particles which impact on an impaction plate may bounce off or be blown off the plate and re-entrained by the gas stream. The particles in a cascade impactor will then not be collected in their proper impaction plate, but will be collected on an impaction plate intended to collect smaller particles. This causes erroneous results to be obtained from an analysis of the deposited particles. Particle bounce increases as the quantity of particles collected under the nozzle increases. A uniform deposit over the entire impaction plate is a desirable feature in reducing particle re-entrainment.

One method used to reduce particle bounce or re-entrainment is to coat the impaction plate with a sticky substance. Once a uniform layer of particles has been collected on the sticky substance, the particles which impact on the impaction plate will bounce from the previously collected particles and not come in contact with the sticky substance. Another method which is used to reduce the bounce of particles is to move the impaction plate each time a particle impaction area becomes loaded with particles or to continuously move the impaction plate. A slotted cascade impactor, the Lundgren impactor, impacts the particles on the surface of a rotating drum. There is no attempt to have uniform deposit of particles on the impaction surface of the drum. Another method to reduce bounce is to move a glass microscopic slide relative to the nozzle. The purpose of moving the slide is to obtain a time resolution of the particles being sampled.

In the field of aerosol science it is advantageous to be able to determine the elemental analysis of the particles which are collected on the impaction plate. One device which is used in this type of study is the x-ray fluorescent analyzer. It is desirable that particles be distributed uniformly in the area illuminated by x-ray, which is typically about 4 cm in diameter. One method of uniformly distributing the particles is filtering the particles from the air stream by a filter. Size classification of particles can be obtained by passing the particles through a dichotomous impactor which divides the particles into two size ranges in the airborne state. The particles are then filtered from the air streams. This classifies the particles into two ranges, one larger and one smaller than the cut-off size of the impactor. Cascade impactors deposit particles in an uneven distribution. Thus, the deposits of particles on the plates of a conventional cascade impactor are not feasible for use with the x-ray fluorescent analyzer. However, if a cascade impactor would collect particles uniformly on the impactor plate, x-ray fluorescent analysis of the deposits would be uniform.

SUMMARY OF INVENTION

The invention is an inertial impactor apparatus useable for collecting and classifying aerosol particles. Aerosol particles are commonly classified by their aerodynamic diameter with cascade inertial impactors. The collected particles are in the form of deposits on impaction plates. The impaction plates are manually removed from the impactor and transported to the laboratory for gravimetric or chemical analysis. Manual operations of removing the impaction plates from the impactor are time consuming and provide opportunity for damage of the deposited particles and erroneous results. This is critical when small quantities of particles are collected. The impactor apparatus of the invention minimizes the handling of the impaction plates and provides for greater reliability of data. The invention is a two-part assembly which can be separated with a minimum of time and work in the field without removing the impaction plates and damaging the particles deposited on the plates.

It is desirable in some tests to have the particles on the impaction plates uniformly distributed over specific areas. When the particles are collected over a selected area, larger quantities of particle mass can be collected on an impaction orifice due to the phenomena of particle bounce and re-entrainment becomes significant. Uniform deposits of particles on impaction surfaces are desirable for certain types of analysis techniques, such as x-ray fluorescence. X-ray fluorescence is a procedure used to determine the elemental makeup of the impacted particles.

The impactor apparatus of the invention has a nozzle assembly and an impaction plate assembly. The impaction plate assembly can be removed in a one step operation from the nozzle plate assembly. A cover replaces the nozzle assembly on the impaction plate assembly to protect the impaction plate and the particles deposited thereon. The cover also facilitates the transportation of the impaction plate assembly to the analysis site.

The individual impaction plates on the impaction plate assembly are not handled so that the deposited particles cannot be damaged. A second impaction plate assembly having clean plates is attached to the nozzle assembly for a subsequent test. This is a simple one step operation that can be performed in the field. The accuracy capabilities of micro-balance can be utilized with the impaction plates made with the impactor apparatus of the invention. The impactor plates do not have to be handled from the time the tar weight is taken in the laboratory to the time that the data is analyzed in the laboratory after the experiment has been performed. In addition, the uniform deposits of particles over a substantial part of the impaction surfaces of the impaction plates permits the micro-balance to accurately weigh small amounts of deposited particles.

In one form of the impactor apparatus, the impaction plate assembly carries a plurality of impaction plates. The nozzle assembly and plate assembly has a plurality of separate chambers that surround each impaction plate. A plurality of nozzles are located in series in a continuous passage to direct particles in sequence to the impaction plates to form a cascade impactor. The nozzles of the nozzle assembly have orifices of decreasing diameters to classify the deposited particles into different size ranges.

In another form of the impactor apparatus the nozzle assembly has a plurality of nozzles with orifices that direct gas and particles to particle collecting means located on a rotatable table. The particles are deposited in separate bands on the rotating particle collecting means.

In a further form of the impactor apparatus of the invention, uniform deposits of particles over separate areas on the impaction plates are achieved by the use of a large number of holes distributed in such a manner as to produce a uniform deposit of particles on several rotating tables. The tables rotate the impaction plates relative to the nozzles so that the particles are deposited uniformly on the impaction plates. The impaction plate assembly rotatably supports the tables. A drive means, including a motor, is used to rotate the tables. The impaction plate assembly, along with the tables and impaction plate thereon, can be separated from both the nozzle assembly and drive structure for the tables so that the impaction plate assembly can be covered and transported to the laboratory for analysis without the drive structure for the tables. The tables are located in series in the gas flow path adjacent separate nozzles. The orifices of the nozzles decrease in diameter in a downstream direction whereby the deposited particles are classified into different size ranges.

DESCRIPTION OF PREFERRED EMBODIMENTS

Referring to FIGS. 1-4, there is shown the first embodiment of the impactor apparatus of the invention indicated generally at 10. Apparatus 10 is a cascade inertia impactor which collects size classified deposits for gravimetric or chemical analysis. Apparatus 10 is intended for use in the collection, classification and analysis of aerosols.

Figures 1, 4, 5, 9:
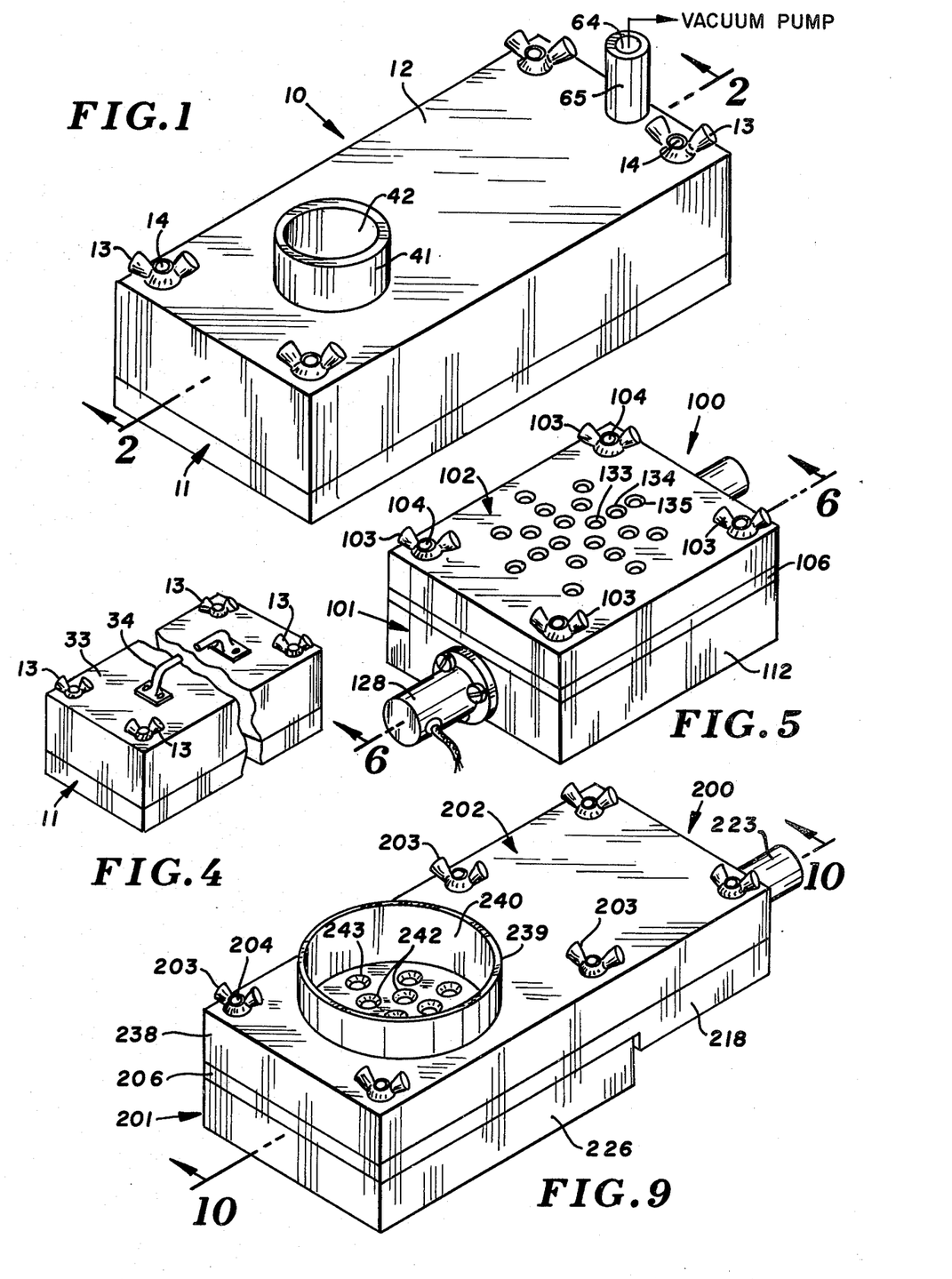
FIG. 1 is a perspective view of a first embodiment of an impactor apparatus of the invention.
FIG. 4 is a foreshortened perspective view of a transport cover attached to the base of the impactor apparatus of FIG. 1.
FIG. 5 is a perspective view of a second embodiment of an impactor apparatus of the invention.
FIG. 9 is a perspective view of a third embodiment of an impactor apparatus of the invention.

Impactor apparatus 10 is a two-part assembly having a base or a plate supporting assembly indicated generally at 11 and a housing or nozzle assembly indicated generally at 12 mounted on base 11. A plurality of releasable fasteners, as wing nuts 13 threaded onto bolts 14, releasably secure housing 12 to base 11. Bolts 14 extend through suitable holes in the corner sections of housing 12 and are threaded into base 11. Other types of releasable fasteners can be used to locate and mount the housing 12 on base 11. The housing 12 can be separated from base 11 by removing the nuts 13 from the bolts 14 and lifting the housing from the top of the base. This can be done in the field with a minimum of time and effort.

Figure 2:
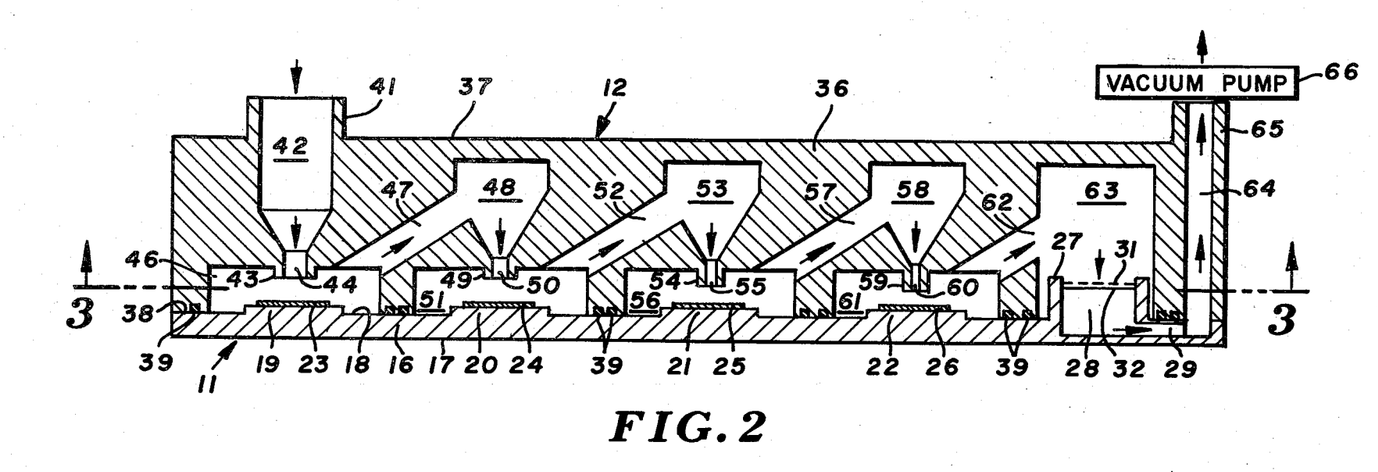
FIG. 2 is an enlarged sectional view taken along the line 2—2 of FIG. 1.

Referring to FIG. 2, base 11 is a generally flat rectangular plate 16 having a flat bottom 17 and a top surface 18. A plurality of upwardly directed circular bosses 19, 20, 21, and 22 are longitudinally spaced along surface 18. Bosses 19-22 are short cylindrical projections that have flat upper circular surfaces that support particle collection means 23, 24, 25, and 26. Particle collection means 23-26 can be particle impaction plates, filters, or glass cover slips, and the like. Particle collection means 23-26 will be hereinafter referred to as impaction plates.

Figure 3:
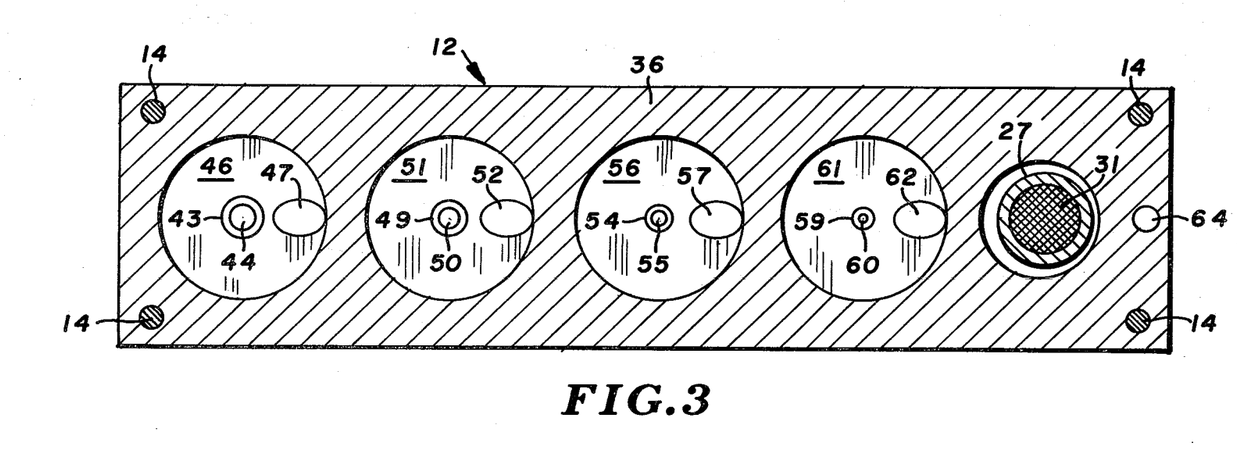
FIG. 3 is a sectional view taken along the line 3—3 of FIG. 2.

As shown in FIGS. 2 and 3, the right or discharge end of plate 16 has an upwardly directed sleeve or collar 27 having a cylindrical passage 28. Passage 28 extends toward the bottom 17 and is open to a lateral exit passage 29. A filter 31 located on a filter support 32 extends across the inlet of passage 28. Filter support 32 is secured to the upper part of sleeve 27.

Base 11, along with impaction plates 23-26 and filter 31, is removed as a unit or an assembly from housing 12 after the test. A new base with impaction plates and a filter can be assembled on housing 12 to conduct the next test. As shown in FIG. 4, the top of base 11 is enclosed with a cover 33. A handle 34 secured to the top of cover 33 is used to facilitate the carrying of cover 33 and base 11 from the test site to the laboratory. Nuts 13 are used to attach cover 33 to bolts 14 extended upwardly from base 11. Base 11 can then be transported to the laboratory for analysis. This procedure allows the impaction plates 23–26 to be weighed in the laboratory before a test and then weighed after the test to determine the mass of the particles deposited on the impaction plates without danger of damage to the deposits of particles. The impaction plates 23–26 during the times of the two weighings will be mounted on bosses 19–22 and at no time will be handled. There is minimum opportunity that the particle mass on the impaction plates will change due to excessive handling or that the deposited particles on impaction plates 23–26 will be damaged through handling. Housing 12 encloses and protects the impaction plates 23–26 during the test. Cover 33 encloses and protects impaction plates 23–26 during the transportation of the base 11 from the test environment to the laboratory.

Referring to FIGS. 2 and 3, housing 12 is a metal body 36 having a top surface 37 and a bottom surface 38. Bottom surface 38 is associated with a plurality of seals 39 that bear against the top surface 18 of base 11. The left or inlet end of body 36 has an upwardly directed sleeve or tubular member 41 having an inlet passage 42 for the gas and aerosol particles. Passage 42 extends downwardly into body 36 to a first nozzle 43 having a round discharge orifice 44. Orifice 44 opens to a chamber 46 surrounding impaction plate 23. Orifice 44 has a circular shape and is located directly above or in longitudinal alignment with the center of the impaction plate 23.

An outlet passage 47 connects first chamber 46 to a cone-shaped chamber 48. Chamber 48 carries gas and aerosol particles to a second nozzle 49 having a second round discharge orifice 50. Nozzle 49 extends downwardly into a second chamber 51 surrounding impaction plate 24. Orifice 50 has a circular hole having a diameter smaller than the diameter of orifice 44. Orifice 50 is located directly above and in longitudinal alignment with the center of impaction plate 24.

An outlet passage 52 connects second chamber 51 with a cone-shaped chamber 53 so that gas and aerosol particles flow from chamber 51 into chamber 53. Chamber 53 carries the gas to a third downwardly directed nozzle 54 having a round discharge orifice 55. Nozzle 54 extends into a third chamber 56 surrounding impaction plate 25. Nozzle 54 is longer than nozzles 43 and 49 and has a discharge end closer to plate 25 than the distance between the discharge ends of nozzles 43 and 49 and plates 23 and 24. Nozzle 54 has an orifice 55 comprising a circular hole having a diameter smaller than the diameter of orifice 50.

An outlet passage 57 connects chamber 56 with another cone-shaped chamber 58 carrying gas and aerosol particles to chamber 58. Chamber 58 carries gas to a fourth nozzle 59 having a round discharge orifice 60. Nozzle 59 projects downwardly into a fourth chamber 61 surrounding impaction plate 26. Nozzle 59 has a length longer than nozzle 54 with the outlet end of orifice 60 being located above impaction plate 26 and positioned closer to the plate 26 than the outlet end of orifice 55. Orifice 60 has a circular hole having a diameter smaller than the diameter of orifice 55.

An outlet passage 62 carries the gas and remaining aerosol particles from chamber 61 to a last chamber 63 located above sleeve 27 so that the gas and aerosol particles that are not collected flow to filter 31. Filter 31 collects the aerosol particles that have not been collected on impaction plates 23–26. The gas flows through the filter 31 through passages 28 and 29 into an upright passage 64 connected with a suitable hose to a vacuum pump 66. Passage 64 passes through an upright tubular projection 65 on body 36.

Orifices 44, 50, 55, and 60 are circular holes that are successively smaller in diameter. Nozzles 49, 54, and 59 have discharge ends that are successively closer to the surfaces of the impaction plates 23–26. Successively smaller particles are collected on impaction plates 23–26 by the use of the successively smaller orifices 44, 50, 55, and 60. The smaller the orifice, the higher the velocity of the gas and particles moving through the orifice.

In FIG. 2, the large particles are collected on impaction plate 23. Successively smaller particles are collected on impaction plates 24, 25, and 26. The size range of particles collected on each of impaction plates 23, 24, 25, and 26 is within a selected range depending on the cut-off characteristics of nozzles 43, 49, 54, and 59. The design of the specific nozzle sizes and lengths for inertial impactors is disclosed by Marple and Willeke in *Fine Particles: Aerosol Generation, Measurement, Sampling, and Analysis*, pp. 411–446 (1976).

In use, vacuum pump 66 operates to draw gas and aerosol particles through impactor apparatus 10. The flow pattern of the gas and aerosol particles carried thereby through apparatus 10 is indicated by arrows. The gas and aerosol or gas suspended particles move through the inlet passage 42 and orifice 44. The larger particles are collected on impaction plate 23, as the orifice 44 is large and the velocity of the particles is low. The aerosol particles and gas then flow consecutively through chambers 48, 53, and 58 with successively smaller classes of particles being deposited on impaction plates 24, 25, and 26. Filter 31 removes all particles that are not collected on the impactor plates 23–26.

Base 11 can be removed from housing 12. Impaction plates 23–26 and filter 31 remain on base 11. Cover 33 is then mounted on base 11 to protect the impaction plates 23–26 and particle deposits thereon and provide a convenient means to transport base 11 to the laboratory. The handling of the impaction plates 23–26 as a unit on the base 11 minimizes the chance that the mass of the particles on the plates 23–26 will be changed due to handling or that the deposited particles on the plates will be damaged. The entire set of impaction plates 23–26 can be readily changed by removing the housing 12 from base 11 and attaching a second base carrying new impaction plates to the housing. This eliminates the practice of changing individual impaction plates in a cascade impactor which may take time in order of several minutes to an hour. The changing of the impaction plates as a unit on the base 11 is advantageous in tests being performed in the field under adverse conditions.

Figures 6, 7, 8, 10:
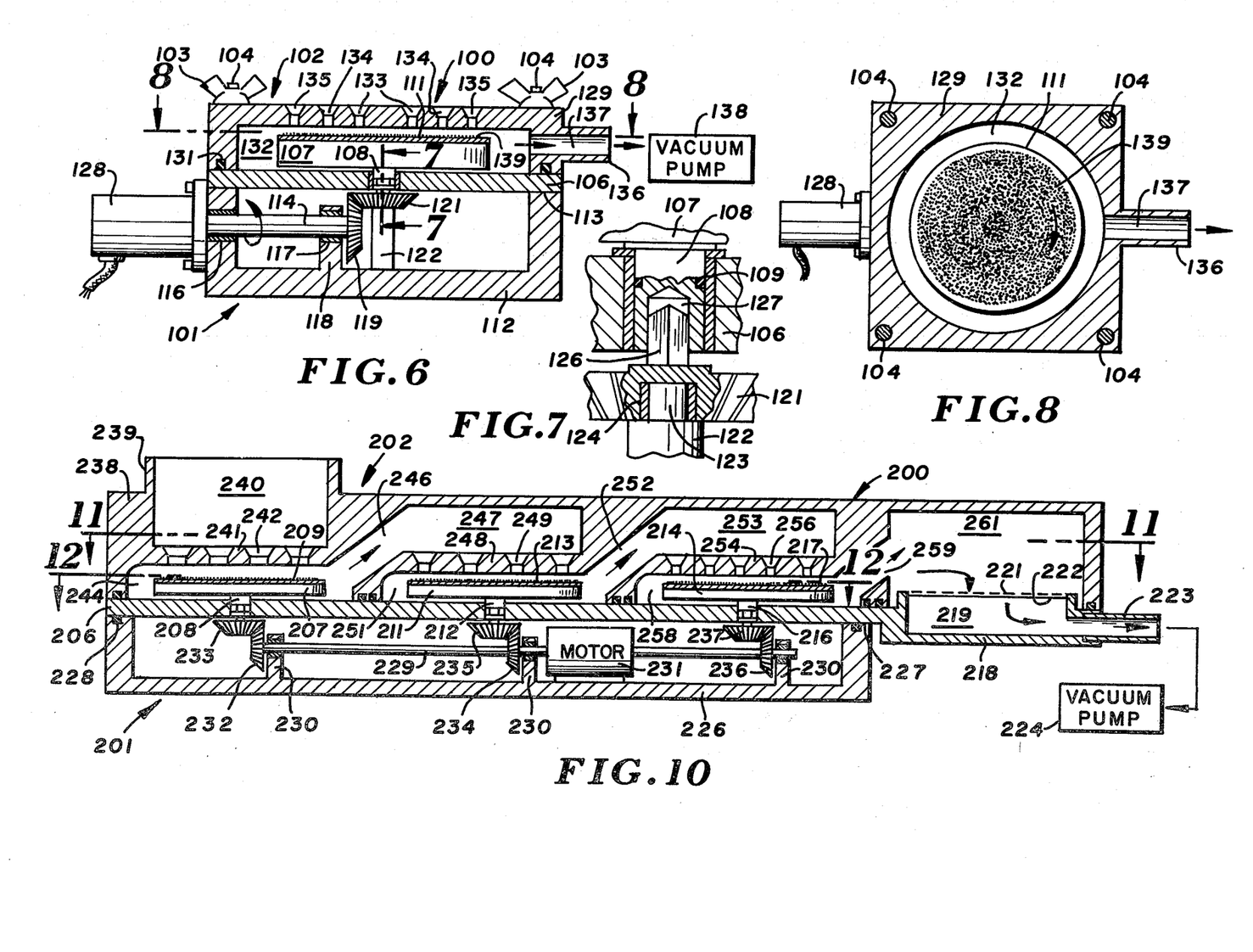
FIG. 6 is a sectional view taken along the line 6—6 of FIG. 5.
FIG. 7 is an enlarged sectional view taken along the line 7—7 of FIG. 6.
FIG. 8 is a sectional view taken along line 8—8 of FIG. 6.
FIG. 10 is an enlarged sectional view taken along the line 10—10 of FIG. 9.

Referring to FIGS. 5 and 6, there is shown the second embodiment of the impactor apparatus indicated generally at 100. Apparatus 100 is a two-piece structure having a base or impactor plate supporting assembly indicated generally at 101 and a housing or nozzle assembly 102. Housing 102 is releasably connected to base 101 with a plurality of nuts or similar fasteners 103 threaded onto bolts 104 attached to base 101. Other structures can be used to releasably attach housing 102 to base 101.

As shown in FIG. 6, base 101 has a plate 106 rotatably supporting a circular table 107. Table 107 has a downwardly directed stem 108 located in a sleeve or bearing 109 positioned in a center hole in plate 106. Table 107 has a top surface supporting a particle collection means 111, as an impaction plate or disc.

Plate 106 is supported on a box or casing 112. Casing 112 has a top surface 113 for supporting an outer peripheral edge of plate 106. A shaft 114 is supported on casing 112 with a pair of bearings 116 and 117. Bearing 117 is carried by an upwardly directed rib 118 attached to the bottom of casing 112. A first bevel gear 119 is mounted on the inner end of shaft 114. Gear 119 drives a second bevel gear 121 rotatably mounted on the upper end of a post 122. Post 122 is attached to the bottom wall of casing 112. As shown in FIG. 7, post 122 has an upwardly directed cylindrical head 123 fitted into a bearing 124 carried by bevel gear 121 to rotatably mount bevel gear 121 on post 122. Bevel gear 121 has an upwardly directed drive finger 126. Finger 126 has a non-circular shape, such as a square or hexagonal cross sectional shape. Finger 126 fits into a pocket or socket 126 in the lower end of stem 108. Finger 126 and socket 127 form a releasable male-female drive connection which enables the plate 106 to be removed from casing 112 so that table 107 and impaction plate 111 can be closed with a cover and transported to a laboratory. An electric motor 128 mounted on casing 122 drives shaft 114. The motor 128 can be battery powered or powered with a conventional source of A.C. electric power. On energization of motor 128, a shaft 114 is rotated, as indicated by the arrow, turning bevel gear 119. This turns gear 121 thereby rotating table 107. Other types of drive units having releasable drive connections can be used to rotate table 107.

Housing 102 has a box-shaped body 129 having a lower surface carrying a peripheral seal 131 adapted to engage the top of plate 106. Nuts 103 clamp body 129 onto plate 106. Body 129 has a chamber 132 surrounding and accommodating table 107. The top of body 129 has a plurality of rings of orifices 133, 134, and 135. As shown in FIG. 5, orifices 133 comprise four orifices in an inner ring or array of orifices. Orifices 134 comprise eight orifices around an intermediate ring of orifices concentric with the inner ring of orifices 133. Orifices 135 comprise an outer ring of eight orifices concentrically located about orifices 134. The radial positions of orifices 133, 134, and 135 are located so that, for any annular area on the top of impactor plate 111, the number of orifices per unit area is constant.

Body 129 has an outwardly directed tubular projection 136 having a passage 137 open to chamber 132. A vacuum pump 138 is connected with a suitable hose to projection 136 whereby pump 138 draws the gas and particles through the orifices 133, 134, and 135 and chamber 132.

As shown in FIG. 8, the particles passing through the orifices 133, 134, and 135 are impacted on the impaction plate 111 mounted on top of table 107. Table 107 is rotated at a substantially constant speed by the operation of motor 128 so that the particles are deposited on impaction plate 111 in a uniform layer of particles 139, as shown in FIG. 8. The table 107 is rotated several rotations for each test. This insures uniform distribution of particles on the upper surface of impaction plate 111. The fluctuations in particle distribution is masked by continuous rotation of the impaction plate 111 with table 107 so that the entire particle collection area of plate 111 is subjected to multiple passes of particles.

Referring to FIGS. 9 and 10, there is shown a third embodiment of the impactor apparatus of the invention indicated generally at 200. Impactor apparatus 200 has a base or impactor assembly 201 attached to a housing or nozzle assembly 202. A plurality of wing nuts 203 threaded on bolts 204 secure housing 202 to base 201. Bolts 204 extend through housing 202 and are anchored in base 201. Other types of releasable connecting structure can be used to attach the housing 202 to the base 201.

Base 201 has a plate 206 rotatably carrying a plurality of tables 207, 211, and 214. Table 207 has a downwardly directed stem rotatably mounted on plate 206. A particle collection means 209, as an impaction plate or disc, is mounted on the top flat surface of table 207. Table 211 has a downwardly directed stem 212 rotatably mounted in plate 206. Particle collecting means 213, as an impaction plate or disc, is mounted on the flat top surface of table 211. Table 214 has a downwardly directed stem 216 rotatably mounted in plate 206. A particle collection means 217, as an impaction plate or disc, is mounted on top of table 214. Tables 207, 211, and 214 rotate about separate upright axes which rotate the particle collection means 209, 213, and 217 in a generally common horizontal plane.

Plate 206 has a box-shaped end section 218 having an outlet chamber 219. A filter 221 carried by a filter support 222 extends across the entrance to the chamber 219. An outlet tube 223 is secured to end section 218 and is open to chamber 219. A hose (not shown) connects outlet tube 223 to a vacuum pump 224.

Impactor assembly 201 has a box-shaped casing 226 having a top peripheral surface or edge 227 engageable with the bottom of plate 206. A seal 228 located in a groove in the top surface 227 engages the bottom of plate 207. A shaft 229 rotatably mounted on a plurality of upwardly directed ribs 230 is connected to a drive motor 231. The motor 231 can be an electric motor coupled to a power source, such as a battery or an A.C. power supply. A first pair of bevel gears 232 and 233 drivably connect shaft 229 to stem 208. A second pair of bevel gears 234 and 235 drivably connect shaft 229 with stem 212. A third pair of bevel gears 236 and 237 drivably connect shaft 229 with stem 216. The bevel gears 233, 235, and 237 can have a male-female releasable drive connection, as shown in FIG. 7, with their respective stems 208, 212, and 216. This allows the plate 206 to be removed from box casing 226 and be attached to a cover for transport to the laboratory. A new plate can be mounted on casing 226 and attached to a nozzle assembly 202 for a second or subsequent test. Motor 231 operates to concurrently rotate tables 207, 211, and 214 at substantially the same constant speed. Other types of drive units can be used to rotate tables 207, 211, and 214.

Nozzle assembly 202 has a body 238. The inlet end of body 238 has a short upwardly directed cylindrical member or sleeve 239 having an inlet passage 240. Passage 240 extends to a bottom wall 241 having a plurality of orifices 242. Orifices 242 are open to a first chamber 244 accommodating table 207. The radial distance from the axis of rotation of disc 207 for each orifice 242 is different so that particles moving through orifices 242 impinge on impaction plate 209 in different areas to form a uniform layer of particles 243A on the collecting surface of plate 209, as shown in FIG. 12. As shown in FIG. 11, orifices 242 are arranged in a spiral pattern.

Other orifice arrangements can be used to achieve a uniform layer of particles on plate 111.

Figure 11:
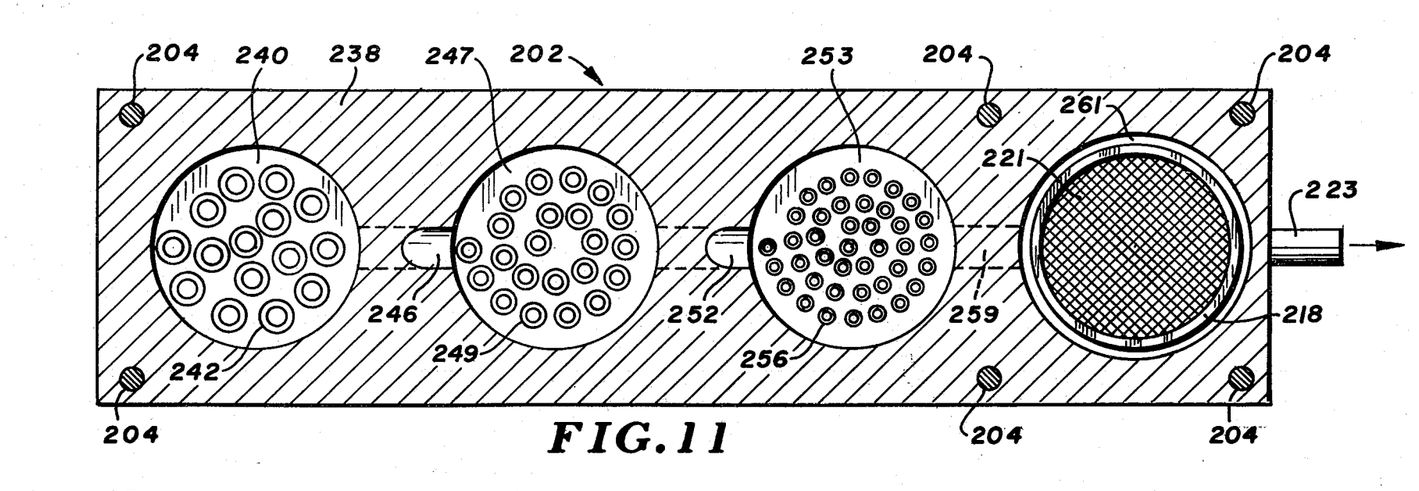
FIG. 11 is a sectional view taken along the line 11—11 of FIG. 10.
Figure 12:
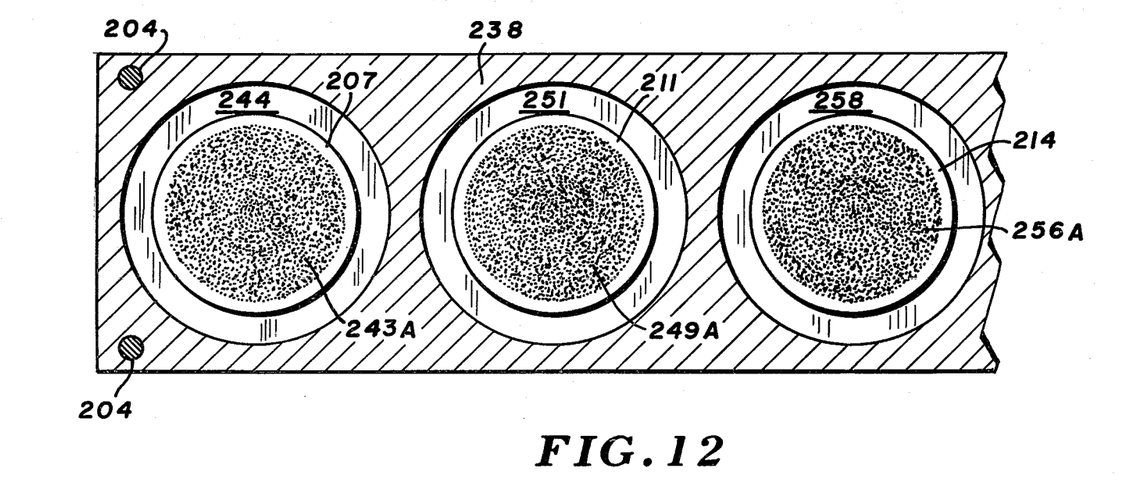
FIG. 12 is an enlarged sectional view taken along the line 12—12 of FIG. 10.
Figure 13:
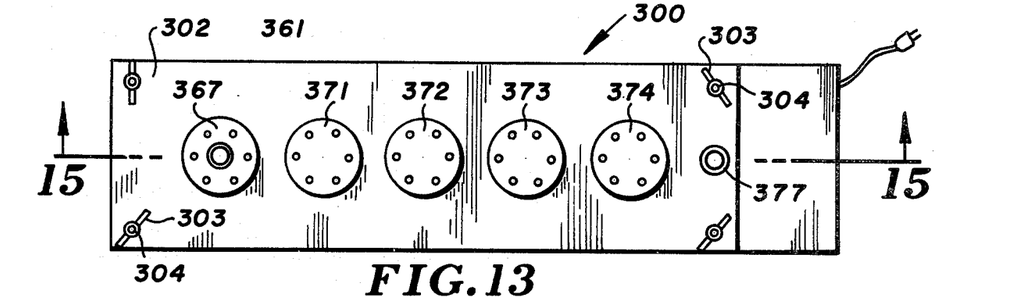
FIG. 13 is a top view of a fourth embodiment of an impactor apparatus of the invention.
Figure 14:
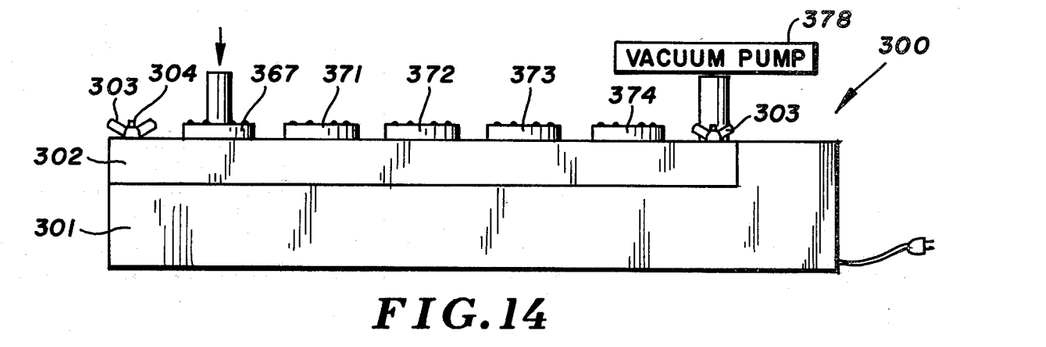
FIG. 14 is a side elevational view of FIG. 13.

A passage 246 connects first chamber 244 with a chamber 247 above a wall 248. Wall 248 has a plurality of orifices 249 open to a second chamber 251 accommodating table 211. Orifices 249 follow a spiral pattern starting from the axis of rotation of table 211. Other orifice locations or arrangements can be used to provide a uniform layer of particles 249A on impaction plate 213. Some of the particles passing through orifices 249 will impinge on impaction plate 213 and collect on the surface thereof as a uniform layer of particles, as shown in FIG. 12. The orifices 249 are smaller in diameter than orifices 242 so that a smaller size range of particles are collected on plate 213.

A passage 252 connects second chamber 251 to a chamber 253. A wall 254 across the bottom of chamber 253 has a plurality of orifices 256. Orifices 256 are open to a third chamber 258 accommodating table 214. The orifices 256 are circular holes that are smaller in diameter than the orifices 249 and are spaced from the axis of rotation of table 214 at separate distances. Orifices 249, as shown in FIG. 11, follow a spiral pattern starting from the center of chamber 247. Adjacent orifices overlap each other to achieve a uniform layer of collected particles 249A on plate 217. The size range of particles collected on impaction plate 214 is a function of the diameter of orifices 256. The smaller the orifices, the smaller collected particle size range. A passage 259 connects third chamber 258 with an outlet chamber 261 located above filter 221.

In use, vacuum pump 224 moves the gas and particles through the nozzle assembly 202, as illustrated by the arrows in FIG. 10. Motor 231 is operated to simultaneously rotate tables 207, 211, and 214. This rotates impaction plates 209, 213, and 217 about separate upright axes. The axes of rotation of tables 207, 211, and 214 are generally parallel to the longitudinal axes of the orifices of the nozzles. The particles flowing with the gas through the first set of nozzles 242 and 243 are directed toward impaction plate 209. A large size range of particles are collected as a uniform layer of particles on impaction plate 209. The gas and particles flow from first chamber 244 through passage 246 into chamber 247. The orifices 249, being smaller in diameter than orifices 242, direct the gas and particles toward the second impactor plate 213. Smaller size particles are collected as a uniform layer of particles 244 on impactor ion plate 213, as shown in FIG. 12. The particles that are not collected on impactor plate 213 move through passage 252 into chamber 253. The orifices 256 deliver the particles from chamber 253 into the third chamber 256 and onto the impaction plate 217. The smaller size particles are collected as a uniform layer of particles 256A on impaction plate 217. The particles that are not collected on any of the impaction plates 209, 213, and 217 flow through passage 259 into outlet chamber 217. These particles are collected on filter 221. After the test is completed, nozzle assembly 202 is removed from plate 206. Plate 206 is removed from casing 216 and enclosed with a cover similar to the cover 33 shown in FIG. 4. The cover and plate 206 carrying the impaction plates 209, 213, and 217 are transported to the laboratory for tests. A new plate 206, with tables carrying impaction plates, is reassembled with casing 226 and nozzle assembly 202 for a subsequent test.

Referring to FIGS. 13 and 14, there is shown a fourth modification of the impactor apparatus indicated generally at 300. Apparatus 300 is a cascade inertia impactor which operates to collect size classified deposits of particles for gravimetric or chemical analysis. Apparatus 300 is utilized in the collection, classification, and analysis of aerosols.

Impactor apparatus 300 is a two-part assembly having a base or particle collecting assembly 301 supporting a nozzle or housing assembly 302. Housing 302 is releasably mounted on base 301 with a plurality of wing nuts 303 threaded onto bolts 304. Other means can be used to locate and mount housing 302 on base 301.

Referring to FIG. 15, base 301 has an elongated top plate 306 supported on a bottom plate 307 with a plurality of spaced cross members 308. Plate 306 has a plurality of linearly spaced cylindrical recesses 309, 310, 311, 312, and 313 open upwardly or to housing 302. Circular discs or turntables 314, 315, 316, 317, and 318 and located in recesses 309–313, respectively. Particle collecting sheet members 319, 320, 321, 322, and 324 are releasably mounted on each of discs 314–318, respectively.

Referring to FIGS. 16, 19, and 20, there is shown an enlarged view of disc 316 supporting particle collection sheet member 321. Sheet member 321 extends over the flat top of disc 316 and is held on disc 316 with a retaining ring 326. Ring 326 is an annular member having an outwardly sloping annular lip 327 spaced from an annular inside groove 328. Disc 316 has an annular outwardly open groove 329 facing groove 328. An O-ring 331 located in groove 329 biases an annular portion of the sheet member 321 into groove 328 to hold the sheet member in firm and flat engagement with the top of disc 316. Retaining ring 326 can be moved in an upward direction forcing lip 327 over O-ring 331 to remove the ring from disc 326 thereby allowing the sheet member 321, along with the particles deposited thereon, to be removed from the impactor apparatus.

As shown in FIGS. 16 and 19, disc 316 has an outwardly directed annular flange 332 located in an enlarged portion or channel 333 of recess 311. Flange 333 rides on an annular portion of a liner 334 covering the inside walls of recess 311. Liner 334 is an anti-friction material, such as Tefflon coating.

Returning to FIG. 15, a drive assembly indicated generally at 336 operates to simultaneously rotate discs 314–318 about separate generally upright axes. Drive assembly 336 includes a power means or motor 337, such as an electric motor. Motor 337 can be provided with a gear reduction unit operable to drive a generally elongated shaft 338 at a substantially constant speed. The output of motor 337 is connected to shaft 338 with a coupling 339. The shaft 338 is rotatably mounted in bearings 341 located in suitable holes in the cross members 308. Shaft 338 is connected to each of the discs 314–317 with separate power transmission means indicated generally at 342, 343, 344, 345, and 346. The power transmission means 342–346 are each operatively associated with a longitudinal support bar 347 mounted on cross members 308.

As shown in FIG. 16, power transmission means 344 is shown in detail. Power transmission means 342, 343, 345, and 346 are identical to the power transmission means 344. Power transmission means 344 has a worm 348 secured to shaft 338. Worm 348 is in driving engagement with a worm gear 349. Worm gear 349 has an upright center hole accommodating a fixed axle 351. Axle 351 is a cylindrical upper end of a bolt 352 threaded into bar 347. A drive magnet 353 is secured to the top of worm gear 349 with an adhesive 354 or similar bonding material. Drive magnet 353 has an upper surface located in contiguous relationship with respect to the bottom of plate 306. A driven magnet 356 is located in the bottom of recess 311 in sliding engagement with liner 334. Magnet 356 is connected to disc 316 with an axial pin 357 and an off center drive pin 358.

In use, motor 337 drives shaft 338. This rotates worm 348 turning worm gear 349 about the upright axis of axle 351. The rotating worm gear 349 turns magnet 353. The magnetic force field between the magnets 353 and 356 rotate magnet 356. Rotating magnet 356 turns disc 316 about its rotational axis.

Figure 15:
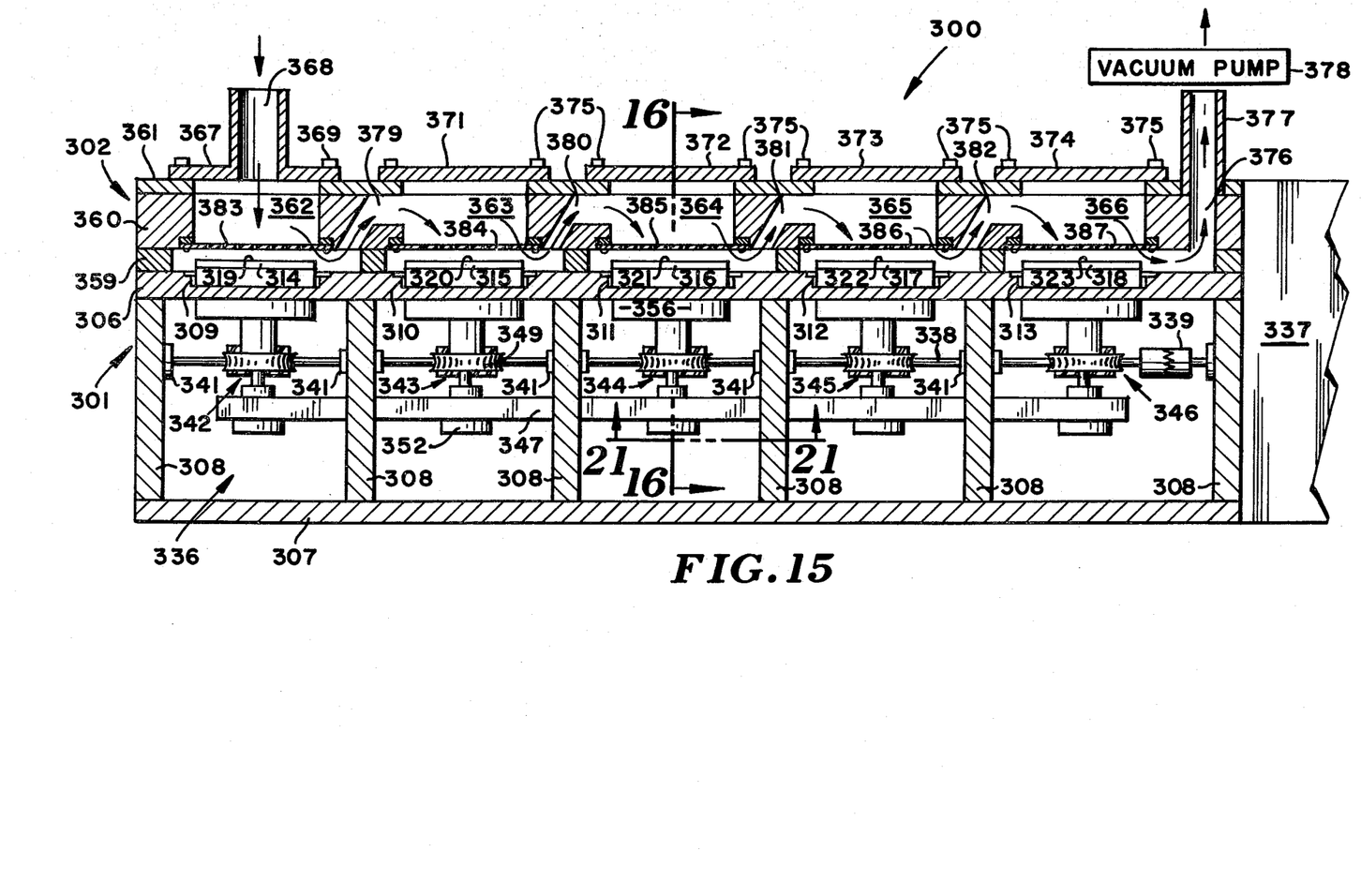
FIG. 15 is an enlarged sectional view taken along the line 15—15 of FIG. 13.

Referring to FIG. 15, nozzle assembly 302 has three side-by-side plates 359, 360, and 361 that are secured together to provide a sandwich plate assembly. The plate assembly has five generally cylindrical chambers 362, 363, 364, 365, and 366 axially aligned with discs 314–318, respectively. A first cap 367 is mounted on top plate 361 over first chamber 362. Cap 367 has an inlet passage 368 allowing aerosol to flow into chamber 362. Cylindrical covers 371, 372, 373, and 374 are secured to plate 361 with bolts 375 which cover chambers 363, 364, 365, and 366, respectively. Cap 367 can be substituted for one of the covers 371–374 to change the number of stages of the cascade impactor apparatus. Plates 359 and 360 have an outlet passage 376 in communication with chamber 366. An outlet tube 377 mounted on plate 361 carries the gas from outlet passage 376 into a vacuum pump 378.

The nozzle assembly plate 360 has a plurality of passages that interconnect adjacent chambers 362–366. A first passage 379 connects the lower portion of chambers 362 with an upper portion of chambers 363. A second passage 380 connects the lower portion of chamber 363 with the upper portion of chamber 364. A third passage 381 connects the lower portion of chamber 364 and upper portion of chamber 365. A fourth passage 382 connects the lower portion of chamber 365 with the upper portion of chamber 366. The gas and particle flow through the inlet passage 368 through the chambers 362–366 and passages 379–382 are shown by arrows in FIG. 15.

Figures 17, 18, 19, 20, 21:
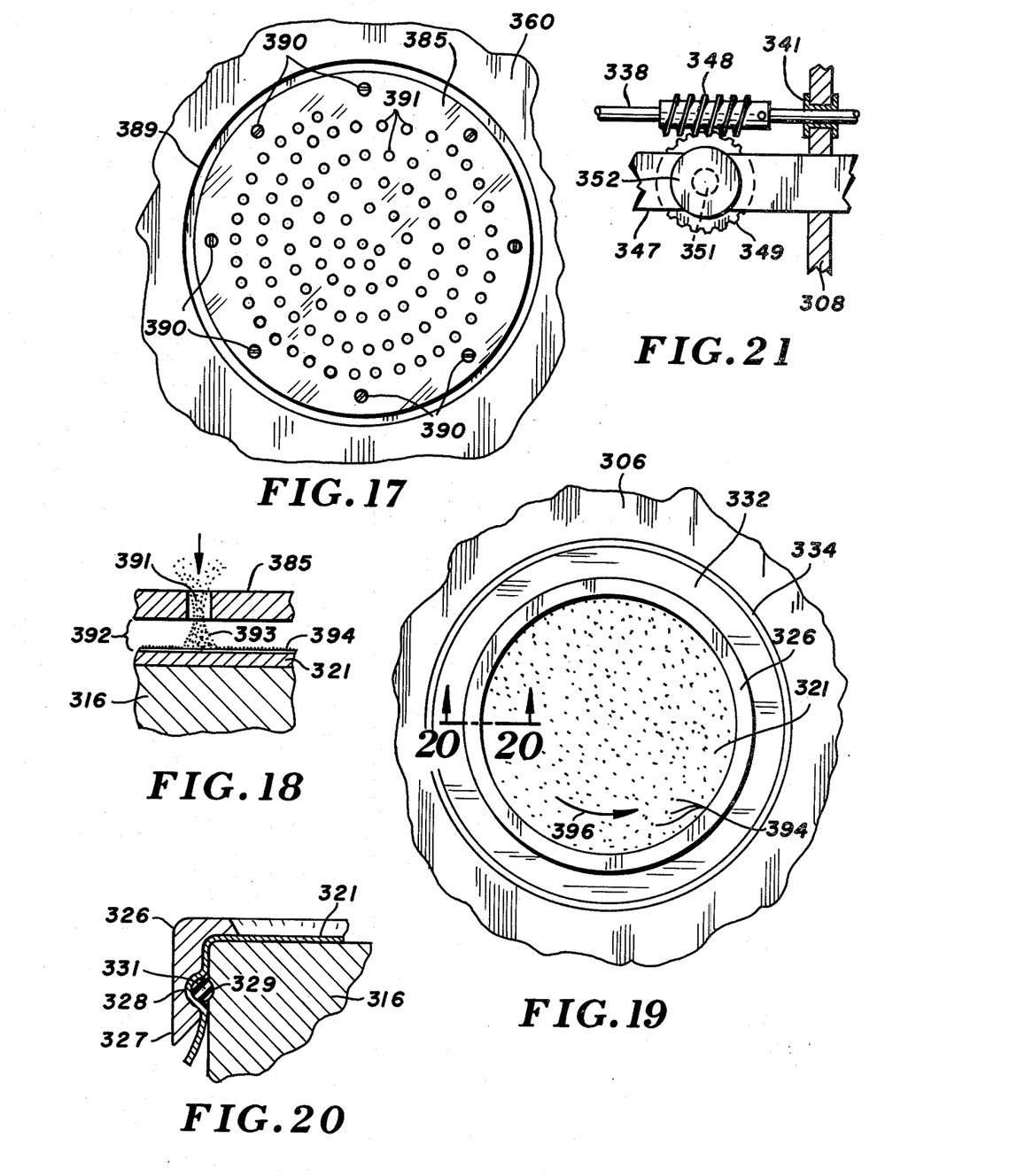
FIG. 17 is an enlarged sectional view taken along the line 17—17 of FIG. 16.
FIG. 18 is an enlarged sectional view taken along the line 18—18 of FIG. 16.
FIG. 19 is an enlarged sectional view taken along the line 19—19 of FIG. 18.
FIG. 20 is an enlarged sectional view taken along the line 20—20 of FIG. 19.
FIG. 21 is an enlarged sectional view taken along the line 21—21 of FIG. 15.

Each chamber 362–366 is separated with a nozzle plate 383, 384, 385, 386, and 387, respectively. The nozzle plates 383–387 are mounted on the plate 360 and extend over the turntables 316–318. Each nozzle plate 383–387 has a plurality of holes or orifices arranged so that substantially even layers of particles are collected on particle collecting sheet members 319–324. The orifices in the plates 383–387 decrease in size with the larger orifices being in plate 383 and the smallest orifices being in plate 387. The hole arrangement in the plates 383–387 can be a spiral pattern, as shown in FIG. 17. Other arrangements of orifices in the plates 383–387 can be used to achieve an even distribution of particles on sheet members 319–324. The size and shape of the orifices can be changed.

Figure 16:
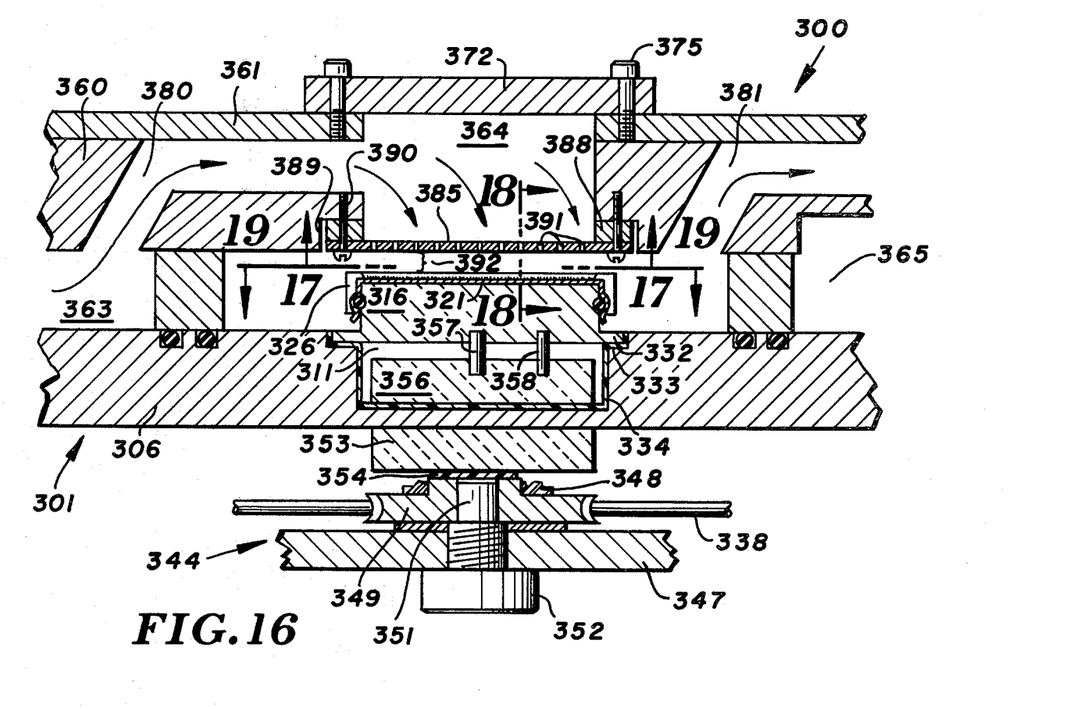
FIG. 16 is an enlarged sectional view of a part of the apparatus of FIG. 15.

Referring to FIG. 16, nozzle plate 385 is mounted on an annular spacer member or ring 388 located in a recess 389 in plate 360. A plurality of bolts 390 secure plate 385 and ring 388 to plate 360. The nozzle plate 385 is located across chamber 364 and above turntable 316. The plate 385 is positioned generally parallel to the top surface of the turntable 316. The nozzle plate 385 has a plurality of holes or orifices 391. As shown in FIG. 17, holes 391 are in a spiral arrangement or pattern. The pattern has a center hole and additional holes located along a spiral line generated from the center of plate 385. As shown in FIG. 18, holes 391 have straight cylindrical side walls and are spaced a distance 393 above sheet member 321. The particles 393 flowing through holes 391 impact on sheet member 321. The particles are collected on sheet member 321 as a substantially uniform layer of particles 394. As shown in FIG. 19, the layer of particles 394 is collected on sheet member 321, as sheet member 321 rotates with turntable 316 in the direction of the arrow 396. The power transmission means 344 driven by the motor 337 operates to rotate turntable 316 at a subtantially constant rotational speed. The turntable 316 is rotated several revolutions for each test. This insures a substantially uniform layer of particles 394 on sheet member 321.

Power transmission means 344 operates to simultaneously rotate turntables 314–318 and the particle collecting means 319–323 mounted on the turntable at a relatively uniform speed. Vacuum pump 378 draws gas and particles through the passages and orifices of the plates 383–387. The orifices of the plates 383–387 being consecutively smaller in diameter from plate-to-plate provide a size classification of particles collected as substantially uniform layers on the particle collecting means or sheet members 319–323. The larger particles are collected on sheet member 319 and the smaller particles are collected on sheet member 323. The particles that are not collected and gas exit through passage 376 to vacuum pump 378. After the test is completed, the nozzle assembly plate 302 is removed from particle collecting assembly 301. The sheet members 319–323 can be removed so that the particles thereon can be subjected to analysis. The particle collecting assembly 301 can be covered with a suitable cover and removed to a location, as a laboratory, where the particles are analyzed.

While there is shown and described several embodiments of the impaction apparatus, it is understood that changes in the structure, materials, and impaction collecting means can be made by those skilled in the art within the scope of the invention. For example, the orifices of the nozzles can be square, rectangular, or other shapes. The invention is defined in the following claims.

The embodiments of the invention in which an exclusive property or privilege is claimed are defined as follows:

1. An impactor apparatus for collecting particles entrained in a gas comprising: particle collecting means, base means having means for supporting said particle collecting means, a nozzle assembly mounted on the base means, means releasably connecting the nozzle assembly to the base means allowing the base means to be removed from the nozzle assembly; said base means when removed from the nozzle assembly being adapted to accommodate a cover to enclose the particle collecting means, said nozzle assembly and base means having an enclosed chamber means open to the means for supporting said particle collecting means, said nozzle assembly including nozzle means having at least one orifice with an inlet open to a source of gas and particles and an outlet opened to the chamber means to direct gas and particles toward the particle collecting means, and a gas outlet means opened to the chamber adapted to be connected to means for drawing gas from the chamber whereby gas and particles are moved from the source of gas and particles through the orifice through the chamber, said particles being directed toward the particle collecting means where some of the particles are collected, said means for supporting said particle collecting means including a rotatable table, and means rotatably mounting the table for rotation about an axis extended generally parallel to a longitudinal axis of an orifice of a nozzle means, and means for rotating the table.

2. The apparatus of claim 1 wherein: the means for rotating the table includes a motor, and means drivably connecting the motor with the table.

3. The apparatus of claim 2 wherein: the means drivably connecting the motor with the table includes a releasable drive connection whereby the base means can be removed from the motor.

4. An impactor apparatus for collecting particles entrained in a gas comprising: particle collecting means, base means having means for supporting said particle collecting means, a nozzle assembly mounted on the base means, said nozzle assembly and base means having enclosed chamber means opened to the means for supporting said particle collecting means, said nozzle assembly including nozzle means having a plurality of orifices with inlets opened to a source of gas and particles and outlets opened to the chamber means to direct gas and particles toward the particle collecting means, said means for supporting the particle collecting means includes a rotatable table, means rotatably mounting the table for rotation about an axis generally parallel to the longitudinal axis of an orifice of the nozzle means, means for rotating the table about said longitudinal axis, said orifices being located relative to each other whereby a substantially uniform layer of particles are collected on the particle collecting means during the rotation of said table.

5. The apparatus of claim 4 wherein: the plurality of orifices is located in a generally spiral path generally centered on the axis of rotation of the table.

6. The apparatus of claim 4 wherein: the means for rotating the table includes a power means, and means drivably connecting the power means with the table, said means drivably connecting the power means with the table including a releasable drive means whereby the base means can be removed from the power means.

7. An impactor apparatus for collecting particles entrained in a gas comprising: particle collecting means, base means having means supporting said particle collecting means, a nozzle assembly mounted on the base means, said nozzle assembly and base means having a plurality of enclosed chamber means opened to the means for supporting said particle collecting means, said nozzle assembly including nozzle means and passages connecting adjusting chambers, one of said nozzle means being opened to a source of gas and particles, gas outlet means opened to one of the chambers adapted to be connected to means for drawing gas from said one of the chamber, said gas flow from the source through said nozzles and passages to said one of the chamber, said means for supporting particle collecting means includes a plurality of rotatable tables, means for rotatably mounting each table for movement about a separate axis extended generally parallel to a longitudinal axis of a nozzle means located adjacent a table, means for concurrently rotating said tables, said nozzle means including a plurality of nozzles corresponding in number to the plurality of rotatable tables, each of said nozzle having orifices to direct gas and particles toward the particle collecting means mounted on a table, each of said orifices of each of said nozzles being located relative to each other whereby a substantially uniform layer of particles are collected on the respective particle collecting means during rotation of said tables.

8. The apparatus of claim 7 wherein: the means for concurrently rotating the tables includes a motor, and means drivably connecting the motor with the tables.

9. The apparatus of claim 8 wherein: the means for rotating the tables includes a releasable drive means allowing the base and tables to be separated from each other.

10. The apparatus of claim 7 wherein: the orifices of each nozzle are located in a generally spiral path and are generally centered on the axis of rotation of the table associated with a nozzle.

11. The apparatus of claim 10 wherein: the orifices of adjacent nozzles are consecutively smaller in diameter with the first orifices being the larger diameter orifices and the last orifices being the smaller diameter orifices.

12. The apparatus of claim 7 wherein: the orifices of adjacent nozzle means in the downstream direction being consecutively smaller.

13. An impactor apparatus for collecting particles entrained in a gas comprising: particle collecting means, base means having means for supporting said particle collecting means, a nozzle assembly mounted on the base means, means releasably connecting the nozzle assembly to the base means allowing the base means to be removed from the nozzle assembly, said base means when removed from the nozzle assembly being adapted to accommodate a cover to enclose the particle collecting means, said nozzle assembly including a body having a plurality of nozzle means, a chamber open to each nozzle means, a gas inlet passage in communication with one of the nozzle means, a gas outlet passage, and passage means connecting the chambers in series with the inlet passage and outlet passage, said outlet passage being adapted to be connected to means for drawing gas from the chambers whereby gas and particles are moved through the inlet passage, nozzle means, chambers, and passage means with the particles being collected on the particle collecting means.

14. The apparatus of claim 13 wherein: said base means comprises a generally flat plate, said means for supporting particle collecting means including a plurality of separate bosses for supporting separate particle collecting means, each of said bosses being open to a chamber and longitudinally aligned with respect to an orifice of a nozzle means.

15. The apparatus of claim 13 wherein: the means for supporting particle collecting means includes a rotatable table in each chamber, means for rotatably mounting each table for movement about an axis extended generally parallel to a longitudinal axis of an orifice of a nozzle means, means for rotating the tables, each of said nozzle means comprising a plurality of nozzles spaced at different radial distances from the axis of rotation of the table whereby particles are deposited as a substantially uniform layer of particles on the particle collecting means.

16. The apparatus of claim 15 wherein: the nozzle means are located in series in the passage means, said nozzle means having orifices that decrease in diameter from the first nozzle means to the last nozzle means.

17. The apparatus of claim 15 wherein: the plurality of nozzles of each nozzle means are located in a general spiral path generally centered on the axis of rotation of the table associated with the nozzle means.

18. The apparatus of claim 17 wherein: the nozzle means are located in a series in the passage means, said nozzle means decreasing in diameter from the first nozzle means to the last nozzle means.

19. An impactor apparatus for collecting particles entrained in a gas on particle collecting means comprising: base means having means for supporting particle collecting means, said means for supporting particle collecting means including a plurality of rotatable means, means for rotating the rotatable means, a nozzle assembly mounted on the base means, means connecting the nozzle assembly to the base means, said nozzle assembly and base means having a plurality of separate chambers, each rotatable means being located in a chamber, passage means connecting the chambers in series, said nozzle assembly including a plurality of nozzle means corresponding to the number of chambers, said nozzle means having a plurality of orifices open to each chamber, and the passage means, the orifices of adjacent nozzle means having different cut-off characteristics whereby different size particles are collected on the particle collecting means located in each chamber, said plurality of orifices of each nozzle means being located relative to each other whereby a substantially uniform layer of particles are collected on the particle collecting means located adjacent a nozzle means, gas and particle inlet means to direct gas and particles to the nozzle means, and gas outlet means open to the passage means adapted to be connected to means for drawing gas from the chambers whereby gas and particles are moved from the source of gas and particles through the orifices into the chambers and passage means, said particles being directed by the nozzle means toward the particle collecting means where some of the particles are collected.

20. The apparatus of claim 19 wherein: the plurality of orifices of each nozzle means are located in a generally spiral path generally centered on the axis of rotation of the rotatable means associated with a nozzle means.

21. The apparatus of claim 19 wherein: the rotatable means is a plurality of rotatable tables, and said means for rotating the rotatable means includes means rotatably mounting the tables for rotation about an axis extended generally parallel to a longitudinal axis of an orifice of a nozzle means.

22. The apparatus of claim 21 wherein: the means for rotating the tables includes a motor, and means drivably connecting the motor with the tables.

23. The apparatus of claim 22 wherein: the means drivably connecting the motor with the tables includes releasable drive connecting means whereby the base means can be removed from the motor.

24. The apparatus of claim 22 wherein: the means drivably connecting the motor with the tables includes first magnet means drivably connected to each table and a second magnet means separated from the first magnet means, and means for rotating the second magnet whereby a magnetic field between the first and second magnets rotates the first magnet thereby rotating the particle collecting means associated with each rotatable means.

25. The apparatus of claim 19 wherein: the nozzle means are located in series in the passage means, said nozzle means having circular orifices that decrease in diameter from the first nozzle means to the last nozzle means.

26. The apparatus of claim 19 wherein: the orifices are circular holes, and adjacent holes of the separate nozzle means in a downstream direction have decreasing diameters.

27. In combination: base means of an impactor apparatus for collecting particles, said base means having means for supporting particle collecting means, said means for supporting particle collecting means including at least one rotatable table, means for rotating said table, said base means being adapted to be attached to a nozzle assembly operable to direct gas and particles to the particle collecting means, cover means mounted on the base means enclosing the means for supporting the particle collecting means to protect the particles on the particle collecting means, and means releasably attaching the cover means to the base means.

28. The combination of claim 27 wherein: said base means includes a generally flat plate.

29. The combination of claim 28 wherein: base means includes means for supporting a filter to collect particles that are not collected on the particle collecting means.

30. The combination of claim 27 wherein: the means for supporting particle collecting means includes a plurality of rotatable tables.

31. The combination of claim 30 wherein: base means includes means for supporting a filter to collect particles that are not collected on the particle collecting means.

32. The combination of claim 27 including: handle means on the cover means to facilitate transport of the cover means and base means attached thereto.

33. An impactor apparatus for collecting particles entrained in a gas on particle collecting means comprising: a particle collector assembly having a plurality of rotatable means for supporting particle collecting means, means for simultaneously rotating the rotatable means, a nozzle assembly mounted on the particle collector assembly, said particle collector assembly and nozzle assembly having a plurality of separate chambers, each rotatable means being located in a separate chamber, passage means connecting the chambers in series, said nozzle assembly including a plurality of nozzle means corresponding in number to the chambers, each of said nozzle means having a plurality of orifices open to each chamber, said orifices of each of said nozzle means being located relative to each other whereby a substantially uniform layer of particles are collected on particle collecting means associated with each rotatable means, the orifices of adjacent nozzle means having different cut-off characteristics whereby different size particles are collected on the particle collecting means located in each chamber, gas and particle inlet means connected to the passage means to direct gas and particles to the passage means, and gas outlet means open to the passage means adapted to be connected to means for drawing gas from the chambers whereby gas and particles are moved from the source of gas and particles through the orifices consecutively of the separate nozzle means into the chambers and passage means, said particles being directed by the orifices of each nozzle means toward the particle collecting means supported on the rotatable means.

34. The apparatus of claim 33 wherein: the orifices of each nozzle means are located in a generally spiral path generally centered on the axis of rotation of the rotatable means associated with the orifices of each nozzle means.

35. The apparatus of claim 34 wherein: the orifices of the separate nozzle means in a downstream direction have decreasing diameters.

36. The apparatus of claim 33 wherein: the particle collector assembly includes a plate having a plurality of recesses corresponding to the number of rotatable means, said rotatable means including a circular table located in each recess, said means for rotating the rotatable means including first magnet means located in each recess, means drivably connecting each first magnet means to a rotatable table, sacond magnet means located outside of the plate in general axial alignment with each first magnet means whereby a magnetic field is established between the first magnet means and the second magnet means, means for rotating the second magnet means whereby said magnetic field rotates the first magnet means thereby rotating the rotatable table associated with each first magnet means.

37. The apparatus of claim 36 including: circular clamp means associated with each table for holding a particle collecting sheet member on each table.

38. The apparatus of claim 33 wherein: the orifices of the separate nozzle means in a downstream direction decreasing in size.

* * * * *